United States Patent [19]

Mirowski et al.

[11] E Re. 30,372

[45] Reissued Aug. 19, 1980

[54] AUTOMATIC CARDIOVERTING CIRCUIT

[75] Inventors: Mieczyslaw Mirowski, Baltimore, Md.; Rollin H. Denniston, III, Golden, Colo.; Thomas E. Davis, Duluth, Minn.

[73] Assignee: Medtronic, Inc., Minneapolis, Minn.

[21] Appl. No.: 901,963

[22] Filed: May 1, 1978

Related U.S. Patent Documents

Reissue of:

[64] Patent No.: 3,805,795
Issued: Apr. 23, 1974
Appl. No.: 235,756
Filed: Mar. 17, 1972

[51] Int. Cl.[2] ..... A61N 1/36

[52] U.S. Cl. ..... 128/49 D

[58] Field of Search ..... 128/2 R, 2.05 D, 2.05 P, 128/2.05 R, 2.06 A, 2.06 E, 2.06 F, 2.06 R, 2.1 E, 2.1 R, 404, 419 D, 419 P, 419 PG, 419 R

[56] References Cited

U.S. PATENT DOCUMENTS

| | | | |
|---|---|---|---|
| 2,976,865 | 3/1961 | Shipley | 128/2.05 D |
| 3,144,019 | 8/1964 | Haber | 128/419 PG |
| 3,323,367 | 6/1967 | Searle | 338/5 |
| 3,389,704 | 6/1968 | Buchowski et al. | 128/419 D |
| 3,608,545 | 9/1971 | Novack et al. | 128/2.06 F |
| 3,614,954 | 10/1971 | Mirowski et al. | 128/419 D |
| 3,638,656 | 2/1972 | Grandjean et al. | 128/419 PG |
| 3,680,544 | 8/1972 | Shinnick et al. | 128/419 P |
| 3,716,059 | 2/1973 | Welborn et al. | 128/419 D |
| 3,815,611 | 6/1974 | Denniston | 128/419 D |

OTHER PUBLICATIONS

Schuder et al "Transactions of the American Society for Artificial Internal Organs", 1970, pp. 207–212.

Stratbucker et al, "Rocky Mountain Engineering Society", 1965, pp. 57–61.

*Primary Examiner*—William E. Kamm

*Attorney, Agent, or Firm*—Carl A. Forest; Joseph F. Breimayer; Lew Schwartz

[57] ABSTRACT

Pulse generating apparatus which provides electrical heart-stimulating pulses only in the absence of normal heart activity. If the patient's heart has developed a life threatening arrhythmic condition the inventive apparatus automatically applies an electrical shock to the heart having sufficient magnitude to restore normal heart activity. The inventive apparatus features a redundant heartbeat sensing system which monitors two dynamic characteristics of heart function, for example, heart contraction and EKG. An electrical heart stimulating pulse is delivered to the patient's heart following the elapse of a specified period of time since the sensing of a dynamic characteristic indicative of a normal functional heart. Sensing control is automatically regained following successful heart stimulation, thereby inhibiting the application of further electrical pulses. In the event that the patient's heart fails to resume normal heartbeat action, the inventive apparatus will continue delivering intermittant shocks—a lower energy pulse is applied first followed by higher energy pulses.

1 Claim, 8 Drawing Figures

POWER SUPPLY

CONTROLLER 30

SYSTEM DISABLE 14

AUTOMATIC CARDIOVERTING CIRCUIT

Matter enclosed in heavy brackets [ ] appears in the original patent but forms no part of this reissue specification; matter printed in italics indicates the additions made by reissue.

*This is a divisional reissue application based on U.S. Pat. No. 3,805,795 issued Apr. 23, 1974 on an application Ser. No. 235,756 filed Mar. 17, 1972; a related divisional reissue application is the application Ser. No. 901,962 filed May 1, 1978.*

BACKGROUND OF THE INVENTION

During the past several decades, coronary heart disease has come to occupy the first position among the causes of death in the developed areas of the world. In the United States, for example, this disease is responsible for over one-half million deaths yearly. And of this number, more than half occur suddenly, outside the hospital, and therefore before the patient is able to obtain the necessary medical assistance. Although the precise cause of sudden death in coronary heart disease has not yet been entirely clarified, the available evidence permits the medical field to ascribe death in the majority of these cases to grave disturbances in cardiac electrical activity culminating in ventricular fibrillation.

Another frustrating but related problem is the present inability to deal effectively with lethal and nonlethal arrhythmias outside of a hospital setting. Within the hospital environment, however, recent experience has clearly demonstrated that ventricular fibrillation and its frequent precursor, ventricular tachycardia, are reversible phenomena when prompt cardioversion of the heart is instituted. Under such circumstances, cardiac function can frequently be restored to normal without the patient suffering from residual disability. Unfortunately, however, the present state of the art makes cardioversion very dependent upon a highly specialized medical environment, thus limiting such treatment to fully equipped, modern hospitals.

There is no question that a great need exists for a defibrillator which would be carried by those who are prone to having one of the many life-threatening arrhythmias generally discussed above. Thus, in some patients having coronary heart disease, a fatal outcome from ventricular tachycardia or ventricular fibrillation could be avoided, even in the absence of immediate medical assistance. The first step, of course, is the detection of those prone to suffering from cardiac malfunctions leading to ventricular tachycardia or ventricular fibrillation.

While it is not possible to predict with unerring exactness which patients suffering from coronary heart disease will die from ventricular fibrillation or ventricular tachycardia, several high risk groups of patients can be recognized. For example, patients who have experienced myocardial infarction, even though they may be surviving in good health, run a substantial risk of dying suddenly, a risk several times greater than that associated with the general population. Further, if patients with myocardial infarction have a history of serious ventricular arrhythmias and/or of cardiac arrest, or if evidence of persistent myocardial irritability is present, it may be logically assumed that the risk of sudden death is increased substantially. A patient like those described above would greatly benefit from an automatic defibrillator.

Also, such an automatic defibrillator would be an asset to those patients who have suffered myocardial infarction in the coronary care unit and remain hospitalized in the coronary care unit or some other area of the hospital. Under such circumstances, the defibrillator could be used temporarily for the remainder of the expected hospital stay; or the automatic defibrillator could be permanently implanted for use both in the hospital and after discharge. And another recognizable class of patients particularly in need of an automatic defibrillator is the class composed of those who have not shown prior histories of myocardial infarction but who show severe symptoms of coronary heart disease, such as ventricular arrhythmias resistant to medical treatment or angina pectoris.

From the brief discussion above, there should be little doubt that the possible applications for an automatic defibrillator are numerous. Such an automatic defibrillator has been developed by Medtronic, Inc. and is described in U.S. Pat. application Ser. No. 124,326, filed Mar. 15, 1971, now abandoned by Mieczyslaw Mirowski, et al. and entitled "CARDIOVERTER HAVING SINGLE INTRAVASCULAR CATHETER ELECTRODE SYSTEM."

The automatic standby defibrillator described in the above-identified patent application employs a pressure sensing element attached to a body implantable electrical lead such that it can be positioned within the right ventricle of the heart. Since the pressure in the heart drops severely when the heart goes into the fibrillation state, ventricular fibrillation can be easily detected by monitoring heart pressure. However, several difficulties with measuring heart pressure are encountered. One disadvantage with using pressure as an indicator of the fibrillation state is that the small pressure sensing elements which are suitable for use with body implantable electrical leads are quite expensive. A second disadvantage with using these pressure sensing elements is that they must either be located alongside, on the outer surface, or at the tip of the body implantable electrical lead to obtain accurate pressure readings. Locating the detection means alongside the catheter tends to make the catheter bulky and inflexible. Fibrotic tissue tends to build-up around the sensing element when it is positioned within the heart. This build-up tends to dampen the pressure transducer mechanism, thus giving inaccurate pressure readings. Inaccurate pressure readings may also result when the element is located at the tip and wedged into the apex of the right heart ventricle as the transducer will then, of course, tend to be dampened by the surrounding heart muscle.

The apparatus of this invention uses a single intravascular electrode of the type described in U.S. Pat. application Ser. No. 202,238, filed Nov. 26, 1971, by Rollin H. Denniston, III, entitled "MUSCLE CONTRACTION DETECTION APPARATUS," to perform three functions: namely, (1) detecting heart contractions; (2) detecting heart electrical activity in the form of R waves; and (3) applying electrical impulses to the heart for cardioverting it.

Thus the apparatus of this invention overcomes many difficulties existent in the prior art devices while providing a compact and practical automatic cardioverting system.

SUMMARY OF THE INVENTION

The present invention relates to a cardioverter, an electronic system which, after detecting one of the above-noted lethal or non-lethal arrhythmias, automatically cardioverts the heart of the user. "Cardioverting" or "cardioversion" as used herein is intended to mean a method of correcting a number of arrhythmic heart conditions including atrial tachycardia, atrial fibrillation, junctional rhythms, ventricular tachycardia, ventricular flutter, and ventricular fibrillation, and any other non-pacing related arrhythmic condition which may be corrected by applying electrical shocks to the heart. Obviously then, "defibrillation" is included in the term "cardioversion" as a method of applying electrical shocks to the heart to defibrillate a fibrillating atrium or a fibrillating ventricle. The system of the present invention may be installed in patients particularly prone to develop ventricular tachycardia and/or ventricular fibrillation, or other types of tachyarrhythmias which may be corrected by cardioverting, either on a temporary or a permanent basis. And, because of extremely small and compact size, the system including both electrodes may be totally and completely implanted under the skin of the patient, or alternatively, may be carried externally, save for the sensing probe carrying the two electrodes.

More particularly, the present invention relates to an automatic cardioverting circuit for monitoring cardiac contraction and sensing when the heart has developed an arrhythmic heart condition, and which then automatically applies a cardioverting shock to the heart of sufficient magnitude to restore effective heart rhythm. The device is adapted to continue delivering intermittent shocks to the heart in the event that the heart fails to return to its normal behavioral pattern, and has the ability of automatically regaining sensing control over a functional heart, thereby insuring that further shocks are inhibited after successful cardioversion has taken place.

The automatic cardioverting circuit comprises two basic subsystems; a sensing system, which continuously monitors heart activity; and a stimulation system which upon receiving a signal from the sensing system applies a cardioverting shock to the heart myocardium through an intravascular electrical lead.

The sensing system of the present invention monitors two dynamic characteristics of the heart and provides an electrical signal corresponding to each heart contraction. The absence of both these characteristics for a predetermined period of time is required before the stimulation system will be activated to transmit a cardioverting shock to the heart. One of the characteristics monitored is the EKG. The EKG is obtained from the electrodes located on the intravascular lead. The second characteristic monitored is muscle contraction. The muscle contraction signal is obtained from a contraction sensing device positioned in the intravascular lead and consisting of a conductive elastomer body having carbon particles imbedded therein. The contraction signal is generated whenever the contraction sensing device is flexed by a heart contraction.

The EKG and the heart contraction signals are fed to a gating device. The gating device will allow a cardioverting shock to be delivered to the heart only if both signals are absent for a predetermined period of time. Thus a heart contraction detected by either the EKG monitoring system or the heart contraction monitoring system is sufficient to prevent a cardioverting pulse from being delivered to the heart. Consequently, each of the monitoring devices provides a back-up signal for the other.

The stimulation portion of the present invention applies energy to the heart in the form of electrical pulses delivered through the electrodes located on the intravascular lead. The application of these electrical pulses to the patient's heart is delayed for a preset period of time (on the order of 15–20 seconds) following the sensing of abnormal heart activity. If normal cardiac action resumes during this period, the application of the cardioverting pulses is automatically inhibited. This delay gives the heart the opportunity to convert spontaneously to normal cardiac rhythm if it is able to do so, and also insures that the cardioverting pulses are applied only when they are needed.

The present invention comprising the sensing system and the stimulation system provides an automatic cardioverting device capable of cardioverting a malfunctioning heart at relatively low energy levels. This device senses when the heart is malfunctioning and then automatically delivers a cardioverting shock to the heart. The device lies dormant during normal heart activity and applies a shock to the heart only when the heart functions become abnormal. This device is extremely compact and features an electrode system, in the form of an intravascular lead, which is totally and completely implantable in the body of a patient. This single intravascular lead is used for sensing the difference between a normally functioning heart and one which is functioning abnormally, and also for transmitting cardioverting shocks to the heart through the electrodes positioned on the same lead. The intravascular lead is also capable of being used for sensing heart conditions requiring heart pacing and for transmitting pacing pulses to the heart.

The invention features a redundant heart contraction sensing system. Two dynamic heart characteristics of the heart function—EKG and heart contraction—are monitored by the invention. A cardioverting shock is transmitted to the heart only following the elapse of a specified period of time since the sensing of a dynamic characteristic indicative of a normally functioning heart. This aids in assuring that cardioverting shocks will be delivered to the heart only when they are needed, and thus largely eliminates the concern over possible heart damage being caused by the delivery of cardioverting shocks to a properly functioning heart.

A disabling feature of the invention further guards against unnecessary cardioverting shocks being applied to the heart. A fracture in the contraction sensor will be automatically detected by a disabling means which will then disable the portion of the circuit which generates and transmits cardioverting shocks to the heart. Therefore, a fracture in the contraction sensor will not result in an unnecessary cardioverting shock being applied to the heart. Further, using an endocardial implantable electrical lead, the invention provides a reliable way of cardioverting a malfunctioning heart without causing serious damage to the heart by the application of high energy densities directly to the heart endocardium. The truncated capacitive discharge waveform used in the circuit of the invention to apply energy to the heart helps minimize the peak and total energy required to cardiovert the heart. Another way the invention minimizes the energy densities applied to the heart is by applying a lower energy pulse first, and then, if that pulse does not restore normal heart functioning, applying cardioverting pulses having higher energy content. The invention also features a counting means which automatically disables the cardioverting circuit after a predetermined number of pulses have been delivered to the heart; thereby preventing cardioverting shocks from being applied when they have little chance of restoring the heart to normal functioning, and could damage the heart.

The invention additionally provides a means for delaying application of the first cardioverting pulse for a period of time, for example, 15 to 20 seconds, following the sensing of abnormal heart functioning. This delay gives the heart the opportunity to convert spontaneously to a normal cardiac rhythm, and also insures that cardioverting pulses are not applied if the heart condition is not critical. There is, of course, no need for the long built-in delay period with the succeeding cardioverting shocks as there is no longer any doubt but that the heart condition is now critical. Accordingly, the succeeding shocks are separated by significantly shorter time intervals.

Other features and advantages of the present invention will be set forth in, or become apparent from, the following description and claims and illustrated in the accompanying drawings, which disclose by way of example and not by way of limitation, the principle of the invention and the structural implementation of the inventive concept.

DESCRIPTION OF THE PREFERRED EMBODIMENT

Figure 1:
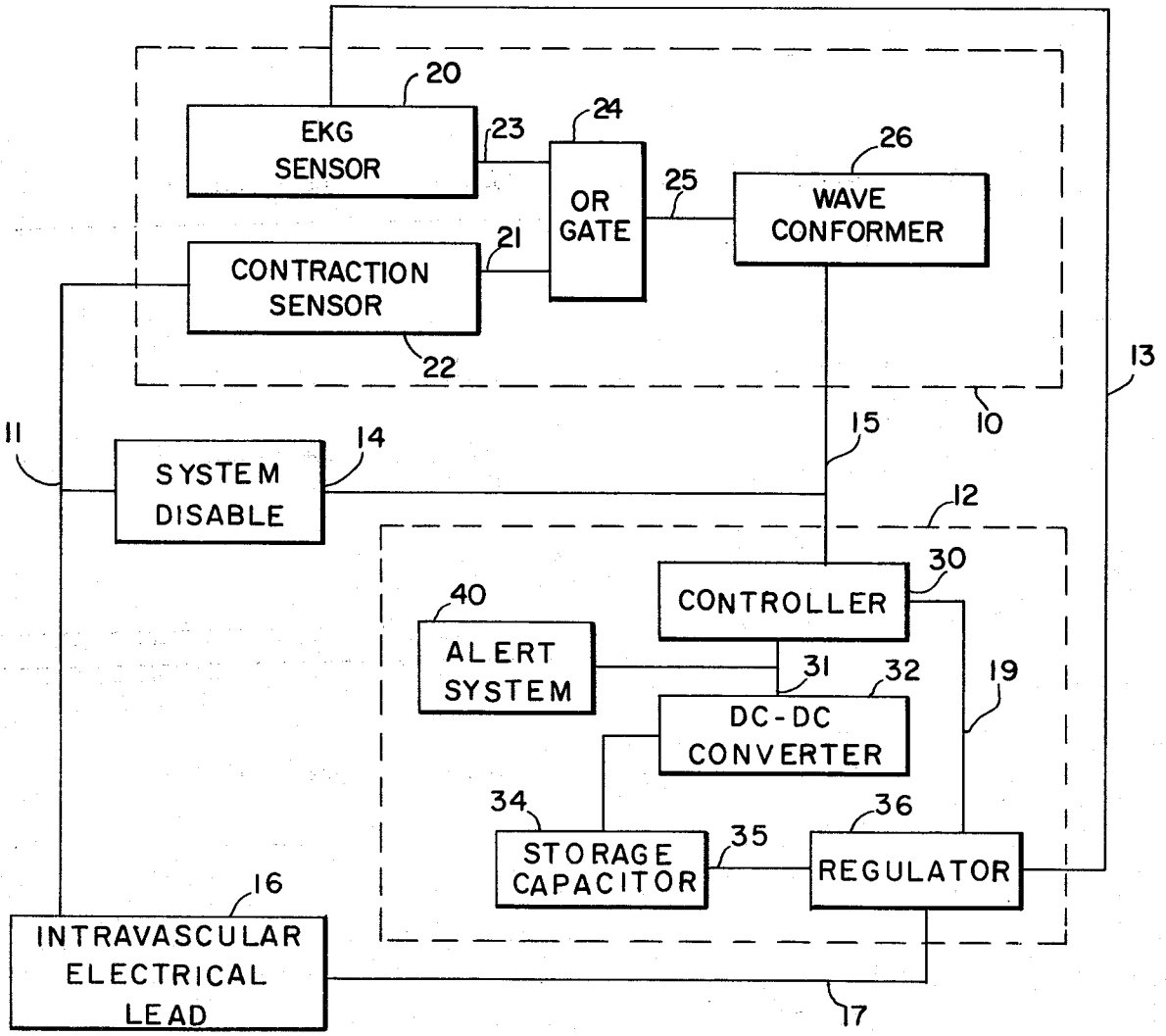
FIG. 1 is a block diagram illustrating basic components of the apparatus provided by this invention.

Referring generally to FIG. 1, the cardioverting apparatus of this invention includes: sensing means shown in block 10 adapted to sense each contraction of the patient's heart; stimulation means shown in block 12 adapted to automatically provide electrical impulses which can be used to cardiovert the patient's heart; an intravascular electrical lead represented in block 16 adapted to detect heart R waves and contractions and to apply electrical impulses to the patient's heart; disabling means shown in block 14 adapted to disable stimulation means 12 whenever electrical lead 16 is rendered inoperative; and a power supply for the system *not* shown in FIG. [4] *1*. Sensing means 10 monitors heart activity and provides an electrical signal to stimulation means 12 which corresponds with each heart contraction. When no electrical signal is received from sensing means 10 for a predetermined period of time, stimulation means 12 is automatically activated to transmit a cardioverting electrical impulse to the heart through lead 16.

Figure 2:
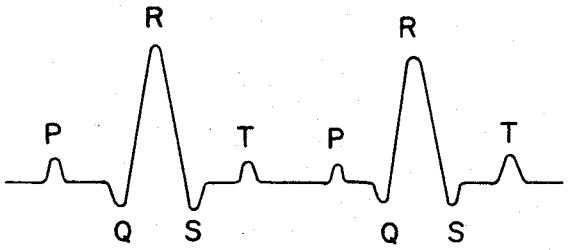
FIG. 2 is a graph indicating the shape of electrical waves produced by the heart during normal heartbeat action.

It will be understood that the normal beating of the human heart produces electrical signals or waves which are representative of the various stages in the occurrence of each heartbeat. Thus a heart beating in sinus rhythm produces electrical waves conventionally identified as P, Q, R, S and T waves, as shown in FIG. 2. The R wave, for example, is representative of a heart's ventricular contraction and can be detected by the electrodes of a conventional electrical intravascular lead of the type commonly used in heart pacing.

An intravascular electrical lead is diagrammatically shown as block 16 in FIG. 1. This block represents an intravascular electrical lead which is adapted to detect the EKG and contractions of the heart and to apply cardioverting electrical pulses to the patient's heart. In a preferred embodiment of this lead the EKG is detected using electrically conductive electrodes; *according to the above-stated companion invention* the heart contractions are detected by an elastomer body which changes impedance whenever it is flexed, as for example, by heart contraction; and the cardioverting electrical impulses are applied to the heart via the same electrodes as used to detect the EKG. However, it will be understood that the above-described embodiment is only one of the many different intravascular lead embodiments which can be advantageously used with the apparatus of this invention.

Figure 3:
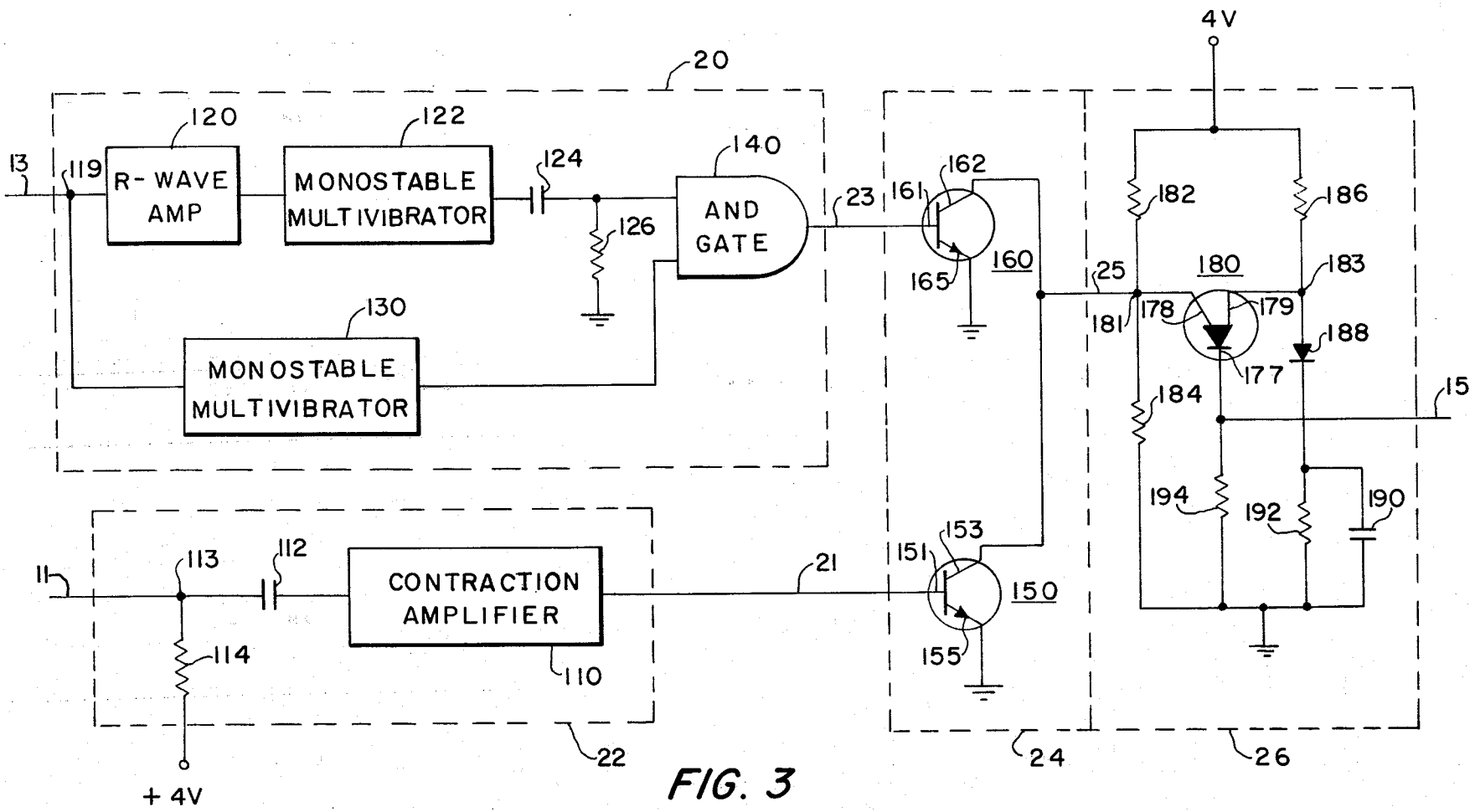
FIG. 3 shows electrical circuitry of the heartbeat sensing means embodied in the apparatus of [this] *the* invention *of the related divisional reissue application Serial No. 901,962 referred to above;*

Sensing means 10 comprising EKG sensor 20, contraction sensor 22, "or" gate 24, and wave conformer 26 is shown in FIG. 3. Sensing means 10, using intravascular electrical lead 16, is adapted to sense R waves and heart contractions and to provide an electrical signal corresponding with each sensed normal heartbeat.

[With] *Turning now to the description of a specific embodiment of the present invention, which embodiment comprises the invention of the above-stated related application, with* reference to FIG. 3, contraction sensor 22 comprises fixed resistor 114, capacitor 112, and operational amplifier 110. One side of fixed resistor 114 is connected to the 4 volt power supply. The other side of resistor 114 is connected to the junction between electrical line 11 and to capacitor 112 for convenience denoted as junction 113. Capacitor 112 is used to AC couple junction 113 to the input side of contraction amplifier 110. The output of amplifier 110 is transmitted on line 21.

Contraction sensor 22 is connected to electrical lead 16 by electrical line 11 and to "or" gate 24 by electrical line 21 and is adapted to provide a usable electrical signal corresponding with each heart contraction.

In a preferred embodiment, electrical line 11 is connected to a conductive elastomer body within electrical lead 16 which changes impedance when flexed by a heart contraction. This change in impedance is easily detectable as it will cause a change in the current flowing from the 4 volt power source through resistor 114, junction 113, electrical line 11, and the elastomer body.

The resulting change in voltage at junction 113 is AC coupled by capacitor 112 to operational amplifier 110 where an electrical output signal in the form of an electrical pulse, is generated in response to the voltage and transmitted to the "or" gate 24 on electrical line 21.

EKG sensor 20 is adapted to amplify each R wave signal detected by the electrical lead 16 corresponding to a normal heartbeat. More specifically, EKG sensor 20 amplifies R waves produced by a human heartbeat, discriminating against the electrical heart waves produced by a heart in fibrillation or otherwise abnormally functioning, as well as the pacer pulses applied using lead 16.

EKG sensor 20 is electrically connected to electrical lead 16 via electrical line 13 and line 17 from stimulation means 12 and to "or" gate 24 by electrical line 23. EKG sensor 20 comprises R wave amplifier 120, compensated monostable multivibrators 122 and 130, capacitor 124, resistor 126, and "and" gate 140. The input side of R wave amplifier 120 and multivibrator 130 are connected to electrical line 13 at junction 119. The output of multivibrator 130 is directly connected to the input side of "and" gate 140, whereas the output side of amplifier 120 is connected to the input side of "and" gate 140 through the series combination of multivibrator 122 and capacitor 124. One side of resistor 126 is connected to the junction between capacitor 124 and "and" gate 140 and the other side is connected to the system ground. The output of "and" gate 140 is transmitted on electrical line 23.

R wave amplifier 120 is an amplifier which operates in the same manner as those commonly used in demand pacer. It is adapted to select and amplify the R waves produced by heartbeats while discriminating against electrical heart waves produced by an abnormally functioning heart. The selection of the R waves is commonly performed by amplitude and frequency filtering.

Monostable multivibrators 122 and 130 are of a conventional design. In a preferred embodiment, the multivibrators used are conventional RCA Monostable Oscillators using COS/MOS Digital Integrated Circuits. The exact multivibrator circuitry used in this preferred embodiment is described and shown schematically in FIG. 9 of RCA Application Note ICAN-6267.

The preferred embodiment multivibrators have two states, a high state and a low state. They are normally in the high state, and are switched into the low state, for a predetermined period of time ($T_\alpha$), upon receipt of an electrical pulse of sufficient magnitude. The period of time ($T_\alpha$) the multivibrator is in the low state and the threshold voltage ($V_1$) of the pulse required to trigger the multivibrator into the low state can, of course, be varied by varying the component values of the circuitry associated with the multivibrators. Accordingly, the output from the multivibrators, upon receipt of a pulse of sufficient magnitude ($V_1$), will be an electrical pulse of a predetermined pulse width ($T_\alpha$).

Capacitor 124 and resistor 126 are electrically connected to multivibrator 122 in such a way that they differentiate the output from multivibrator 122. Thus if multivibrator 122 remains in the high state, there will be no input from multivibrator 122 through the differentiating circuit of capacitor 124 and resistor 126 to "and" gate 140. However, this differentiating circuit will provide "and" gate 140 with a negative spike pulse followed by a positive spike pulse at a time ($T_\alpha$) later when a negative electrical pulse is generated by multivibrator 122.

Gate 140 is a conventional "and" gate. It is adapted so that it will transmit an electrical pulse, if at the time it receives the positive pulse from the differentiating circuit of capacitor 124 and resistor 126, the electrical signal received from multivibrator 130 is in a high state. If at the time the positive spike pulse is received from the differentiating circuit the electrical signal received from multivibrator 130 is in the low state, then gate 140 will not transmit an electrical pulse.

Selecting multivibrators 122 and 130 having the proper threshold voltages ($V_1$) and the proper pulse widths ($T_\alpha$) will allow EKG sensor 20 to differentiate between pacer pulses and R waves. In a preferred embodiment, multivibrator 122 will have a threshold $V_1$ of 10 m-v and a pulse width of $T_\alpha$ of 1 m-sec and multivibrator 130 will have a threshold $V_1$ of 0.5 v and a pulse width of 5 m-sec. R waves from a human heart beating in normal sinus rhythm commonly have a magnitude in the 20 m-volt range when sensed through the intracardiac lead system; whereas pacer pulses are commonly in the 1.0 to 2.0 volt range. Accordingly, a normally produced R wave will be insufficient to trigger multivibrator 130 into its low state but the R wave amplified by amplifier 120 will be sufficient to trigger multivibrator 122 into its low state and thus will cause the differentiating circuitry to supply a positive spike pulse to gate 140 when multivibrator 122 returns to its high state 1 m-sec. later. This positive spike pulse will cause gate 140 to transmit an electrical pulse on line 23 as multivibrator 130 will be in the high state. Conversely, pacer pulses will trigger both multivibrator 122 and multivibrator 130. Since the output of monostable multivibrator 122 is effectively delayed 1 m-sec. by differentiation elements 124 and 126, monostable multivibrator 130 will be in the low state when gate 140 receives the positive pulse from multivibrator 122. Thus gate 140 will not transmit a pulse on line 23.

Gate 24 comprises transistors 150 and 160. The base 151 of transistor 150 is electrically connected to contraction sensor 22 via electrical line 21; the emitter 155 is connected directly to the system ground; and the collector 153 is electrically connected to wave conformer 26 via electrical line 25. The base 161 of transistor 160 is electrically connected to EKG sensor 20 via electrical lead 23; the emitter 165 is connected directly to the system ground; and the collector 163 is electrically connected to the electrical line 25 and the collector 153 of transistor 150.

Gate 24 functions as a conventional "or" gate. Transistors 150 and 160 are normally in the non-conductive state; however, if an electrical pulse from contraction sensor 22 is received at the base 151 of transistor 150, it will render transistor 150 conductive, thus providing a low resistance electrical path from electrical line 25 to ground. Likewise, an electrical pulse from EKG sensor 20 will render transistor 150 conductive; thus providing a low resistance electrical path from electrical line 25 to ground. Consequently, whenever an electrical pulse is received from contraction sensor 22 or EKG sensor 20 or from both, gate 24 will provide a low resistance path from electrical line 25 to ground.

Wave conformer 26 is electrically connected to gate 24 via electrical line 25 and to stimulation means 12 via electrical line 15, and is adapted to conform the electrical signals received from gate 24 into pulses having substantially the same pulse width and amplitude. The conformed electrical pulses received from wave conformer 26 have a predetermined pulse amplitude and width which is sufficient to effect the functioning of stimulation means 12.

Wave conformer 26 comprises a programable unijunction transistor 180 electrically connected in a monostable multivibrator arrangement. Programable unijunction transistor 180 has a gate input 178, an anode input 179, and a cathode 177. This type of transistor is commonly referred to as a PUT in the engineering literature. It is rendered conductive, thereby providing a low impedance from both the PUT anode and gate to its cathode, when the anode voltage exceeds the gate voltage by a specified amount, for example, 0.7 volts.

PUT 180 is connected with its gate 178 electrically connected to junction 181, its anode 179 electrically connected to junction 183, and its cathode 177 electrically connected to electrical line 15. Resistor 194 is electrically connected between electrical line 15 and the system ground. Junction 181—the junction between resistors 182 and 184—is electrically connected to gate means 24 via electrical line 25. Resistors 182 and 184 are connected in series between the 4 volt power supply and ground, thereby forming a voltage divider which establishes the voltage at junction 181 at a predetermined value. Junction 183 is the junction between resistor 186 and diode 188. Resistor 186, diode 188 and the parallel combination of resistors 192 and capacitor 190 are connected between the 4 volt power supply and the system ground. The component values of resistor 186 and 192 and capacitor 190 are chosen such that the voltage at junction 183 is kept at a predetermined value which normally forces PUT 180 into a non-conducting state.

Wave conformer 26 is adapted to provide a pulse having a predetermined amplitude and width in response to each electrical signal received from gate 24. Whenever an electrical pulse is received by gate 24 from contraction sensor 22 or EKG sensor 20 or from both, gate 24 becomes active, providing a low resistance path from electrical line 25 to ground. Junction 181 is electrically connected to electrical line 25 and thus becomes connected to ground via a low resistance path whenever gate 24 is active. Consequently, whenever gate 24 is active, the voltage at junction 181 is decreased and falls to a voltage such that PUT 180 is rendered conductive.

Transistor 180 will remain conductive for a predetermined period of time. This time period is determined by the discharge time of capacitor 190.

Once PUT 180 becomes conductive, capacitor 190 is prevented from discharging through it by diode 188. Consequently, capacitor 190 must discharge through resistor 192. The capacitor 190 and resistor 192 component values are selected such that capacitor 190 discharges at a predetermined rate, thus keeping the voltage at junction 183 sufficiently high to keep PUT 180 conductive for a predetermined period of time. Accordingly, this time period establishes the pulse width of the pulse generated by wave conformer 26. The amplitude of the generated pulse is established by the voltage at which junction 183 is maintained while PUT 180 is conductive. The generated pulse having a predetermined amplitude and width is transmitted to stimulation means 12 on output line 15.

Figure 4:
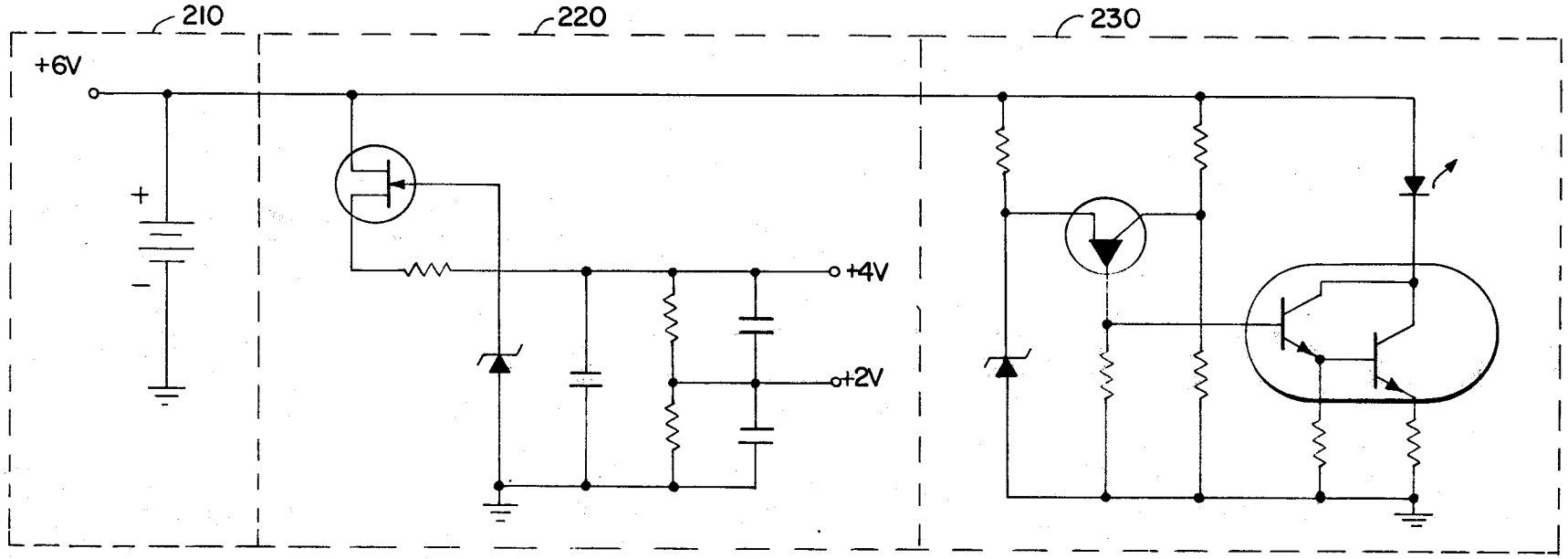
FIG. 4 is a schematic diagram illustrating the power supply and the low battery indicator incorporated in the apparatus of [this] *the above-stated related* invention.

Referring to FIG. 4, the power supply for the cardioverting system is shown schematically. With reference to FIG. 1, the system power supply (not shown) must provide the energy needed to charge storage capacitor 34 as well as providing the energy needed to drive and bias the circuitry of sensing means 10, and the associated circuitry of stimulation means 12. This requires that it have a substantially constant output, as the sensing and stimulation circuitry do not function well when they are driven and biased by a supply that fluctuates significantly; that it be able to supply the relatively large amount of energy required to charge storage capacitor 34; and that it be as compact as possible.

The above stringent requirements are met by the power supply embodiment shown in FIG. 4 which comprises a 6 volt battery 210 which drives a 4 volt supply 220. The 6 volt battery 210, via a DC to DC converter 32 (FIG. 1), supplies the energy needed to charge capacitor 34 (FIG. 1), whereas the 4 volt supply 220 supplies a constant driving and biasing voltage for the circuitry of sensing means 10 and the associated circuitry of stimulation means 12. This particular embodiment prevents fluctuations in the output of the 6 volt battery 210, caused by the drain put on it when the storage capacitor 34 is charged, from affecting the 4 volt source 220 output, provided the output of the 6 volt battery 210 remains above 4 volts.

A low battery indicator 230 is also shown in FIG. 4. The indicator 230 is set so that it is activated whenever the power source 210 output falls below a predetermined voltage level, for example, 4.0 volts, and is used to drive a light emitting diode which indicates that the power source output is below this predetermined level.

Figure 5:
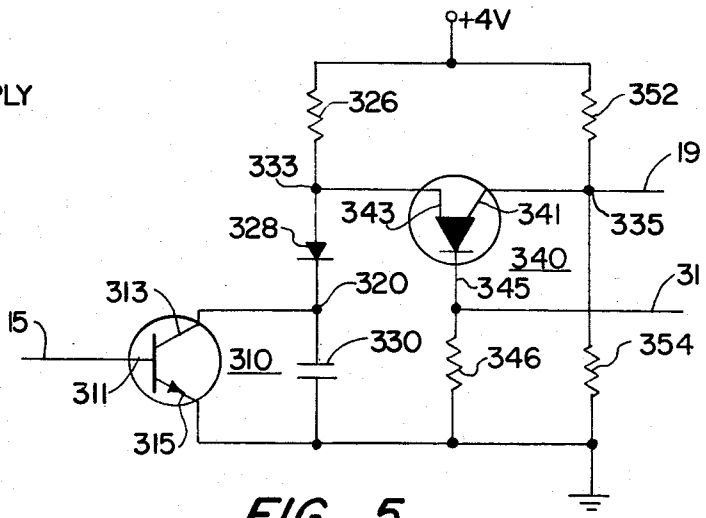
FIG. 5 is a schematic diagram illustrating the control means incorporated in the apparatus of [this] *the above-stated related* invention.

Controller 30 is shown schematically in FIG. 5. It comprises programable unijunction transistor 340, transistor 310, diode 328, capacitor 330 and resistors 326, 352, 354 and 346. Programable unijunction transistor 340 has a gate input 341, an anode input 343, and a cathode 345. This type of transistor is commonly referred to as a PUT in the engineering literature. It is rendered conductive, thereby providing a low impedance from both the PUT anode and gate to its cathode when the anode voltage exceeds the gate voltage by a specified amount, for example, 0.7 volts. Resistors 352 and 354 are electrically connected in series between the 4 volt power source and the system ground. Resistor 326, diode 328, and capacitor 330 are likewise electrically connected in series between the 4 volt source and the system ground. The junction between resistors 352 and 354, designated junction 335, is electrically connected to gate 341 of PUT 340—the junction between resistor 326 and diode 328 designated junction 333, is electrically connected to anode 343 of PUT 340. The cathode 345 of PUT 340 is electrically connected to electrical line 31 and also to the system ground through resistor 346. Transistor 310 has its collector 313 electrically connected to the junction between diode 328 and capacitor 330, designated junction 320; its emitter 315 electrically connected to the system ground; and its base 311 electrically connected to sensing means 10 via electrical line 15.

The junction 335 voltage is maintained constant as it is the junction between resistors 352 and 354 which form a voltage divider; whereas the junction 333 voltage varies depending upon the charge on capacitor 330. Capacitor 330 is charged by the 4 volt energy source through the series connection of resistor 326 and diode 328. In a preferred embodiment the component values of capacitor 330, diode 328 and resistor 326 are chosen so that it takes approximately 5 seconds to charge capacitor 330 to the predetermined level where it will render PUT 340 conductive. Diode 328 prevents capacitor 330 from discharging through PUT 340. Since transistor 310 is connected across capacitor 330 to the system ground, whenever transistor 310 is rendered conductive capacitor 330 rapidly discharges to ground. However, transistor 310 is in the non-conductive state unless it receives an electrical signal from sensing means 10 on electrical line 15. This signal comes from wave conformer 26 and is of sufficient pulse amplitude and width to keep transistor 310 on long enough for capacitor 330 to totally discharge.

Consequently, whenever an electrical signal is received from sensing means 10, capacitor 330 will discharge, rendering PUT 340 non-conductive. PUT 340 will remain non-conductive for at least 5 seconds; longer if another pulse is received from sensing means 10 during that five second interval. However, when PUT 340 becomes conductive, it will remain conductive until a pulse is received from sensing means 10. This is the case since capacitor 330 cannot discharge except through transistor 310, and thus will remain at substantially the same voltage until transistor 310 is rendered conductive by a pulse from sensing means 10.

Figure 6:
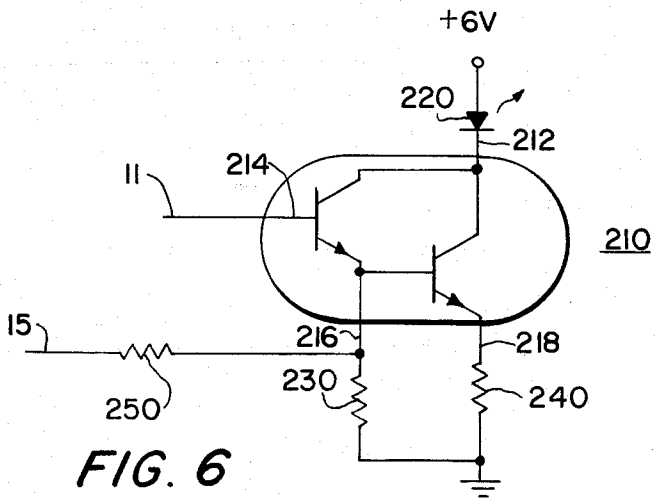
FIG. 6 is a schematic diagram illustrating the system disabling means incorporated in the apparatus of [this] *the above-stated related* invention.

System disable 14, shown schematically in FIG. 6, continuously monitors the contraction sensing circuitry of intravascular lead 16. It is adapted and connected so that if an open circuit should occur in the contraction sensor, whether due to a break in lead 16 or in the sensor itself, a visual alarm is activated and the controller 30 is clamped so that it is non-conducting.

System disable 14 comprises conventional Darlington amplifier 210, visual alarm 220 in the form of a light emitting diode, and resistors 230 and 240. Visual alarm 220 is electrically connected between the six volt power supply and input 212 of amplifier 210. Amplifier 210 is electrically connected to the contraction sensor of intravascular lead 16 at input 214 via electrical line 11. The two outputs 216 and 218 from amplifier 210 are electrically connected to the system ground through resistors 230 and 240 respectively. Output 216 is additionally electrically connected to controller 30 via electrical line 15.

When an open circuit occurs in the contraction sensing circuit, system disable 14 will prevent stimulation means 12 from applying a cardioverting pulse to the patient's heart. Specifically, when the contraction sensing circuit is broken, the increase in voltage at input 214 will render amplifier 210 conductive. Amplifier 210 will remain conductive until the break in the contraction sensing circuit is repaired. When amplifier 210 conducts, visual alarm 220 will be activated and an electrical signal will be transmitted to controller 30 on electrical line 15. This electrical signal clamps controller 30 in an off state thereby preventing controller 30 from activating DC—DC converter 32 and thus prohibiting a cardioverting pulse being applied to the patient's heart.

Figure 7:
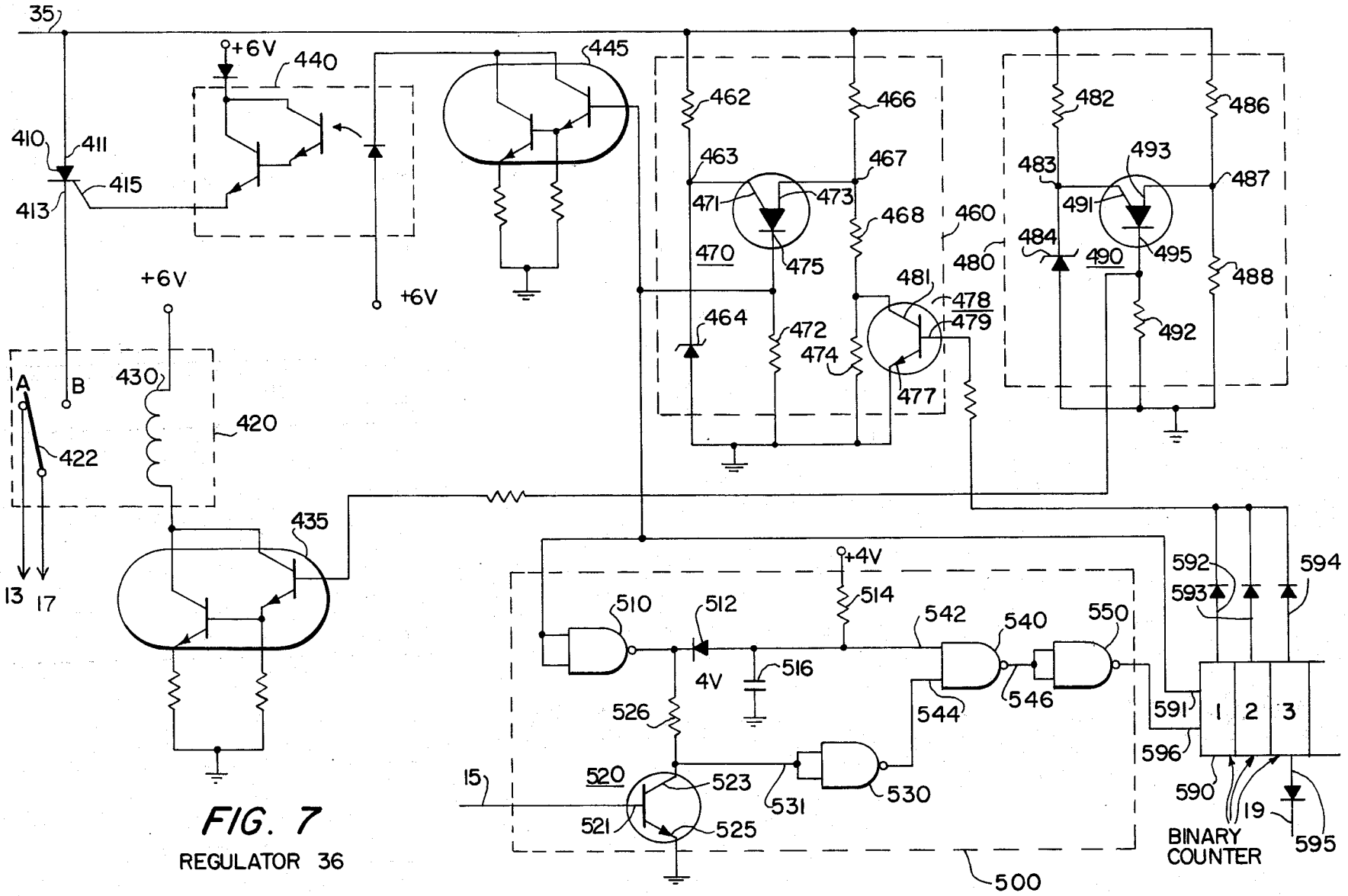
FIG. 7 is a schematic diagram illustrating the regulating means incorporated in the apparatus of [this] *the above-stated related* invention.

Regulator 36 is shown schematically in FIG. 7. It controls the application of stimulating pulses to the heart. That is, it allows stimulating pulses to be transmitted from capacitor 34 to the heart only when they have an energy content which is sufficient so that they are likely to be able to stimulate heart activity, but not so great so that it is likely to cause permanent heart damage. The energy content of the applied pulses is determined by regulator 36. Specifically, regulator 36 is adapted to apply a relatively low energy cardioverting pulse first, and then if that does not restore normal heart function to apply a higher energy cardioverting pulse.

Referring generally to FIG. 7, regulator 36 will allow energy from capacitor 34 to be applied to the heart when silicon controlled rectifier (SCR) 410 is in the conductive state and reed relay 420 is in the position designated position B. If SCR 410 is in the nonconductive state or reed switch 422 is in the position designated position A, then energy cannot be applied from capacitor 34 to the heart. SCR 410 and reed switch 422 (when it is in position B) are electrically connected in series between electrical line 35 and electrical line 17—electrical line 17 is electrically connected to intravascular lead 16 so that it is capable of transmitting a cardioverting pulse to the heart. Reed switch 420, when it is in position A, electrically connects EKG sensor 20 to lead 16. Specifically, reed relay 420 electrically connects EKG sensor 20 via electrical line 13 to lead 16 via electrical line 17. Accordingly, EKG sensor 20 is electrically disconnected from lead 16, whenever reed switch 422 is capable of transmitting energy from capacitor 34 to lead 16 (position B). Conversely, EKG sensor 20 is electrically connected to lead 16 whenever reed switch 422 is incapable of transmitting energy from capacitor 34 to lead 16 (position A). This isolates EKG sensor 20 from the cardioverting pulse being applied to the heart.

Reed relay 420 is of conventional design. It comprises a coil 430 which is adapted to mechanically move switch 422 from one terminal to another. Coil 430 is electrically connected at one end to 6 volt power supply and at the other to a conventional Darlington amplifier 435. When amplifier 435 is active, current flows from the 6 volt source through coil 430. This causes reed switch 422 to mechanically move from terminal A to terminal B.

SCR 410 is connected with its input 411 electrically connected to electrical line 35; its output 413 electrically connected to terminal B of reed switch 422; and its base 415 electrically connected to a Photo-Darlington relay 440. In a preferred embodiment relay 440 is a Monsanto MCA2 solid state relay. This relay is particularly adapted to isolate SCR 410 from the other circuit components of regulator 36. It is capable of rendering SCR 410 conductive whenever it becomes active. SCR 410 will remain conductive as long as the current path through it is not interrupted. Specifically, SCR 410 will remain conductive, once it is rendered conductive, as long as reed switch 422 is at position B or until the potential on line 35 is essentially zero.

The two voltage level detectors shown generally at 460 and 480 control SCR 410 and reed relay 420. More particularly, voltage level detector 460 must be active to render SCR 410 conductive and voltage level detector 480 must be active to move reed switch 422 to position B. Accordingly, since SCR 410 must be conductive and switch 422 must be at position B for energy to be transferred to the heart in the form of cardioverting pulses, detectors 460 and 480 effectively control the application of the cardioverting pulses.

The elemental unit denoted level detector 480 comprises programable unijunction transistor 490, zener diode 484 and resistors 482, 486, 488 and 492. Programable unijunction transistor (PUT) 490 has a gate input 491, an anode input 493, and a cathode 495. PUT 490, like PUT 320 of controller 30 and PUT 180 of wave conformer 26, is rendered conductive thereby providing a low impedance from both the PUT anode and gate to its cathode when the anode voltage exceeds the gate voltage by a specified amount, for example, 0.7 volts. Resistor 482 and zener diode 484 are electrically connected in series between electrical line 35 and the system ground. Resistors 486 and 488 are likewise electrically connected in series between electrical line 35 and the system ground. The junction between resistor 482 and diode 484, designated junction 483, is electrically connected to the gate 491 of transistor 490—the junction between resistor 486 and 488, designated junction 487, is electrically connected to the anode 493 of transistor 490. The cathode 495 of transistor 490 is electrically connected to Darlington amplifier 435 and also to the system ground through resistor 492.

Level control 480 is voltage sensitive. It will be rendered active when the voltage on electrical line 35 is above some predetermined level, for example, 550 volts and will remain active as long as the voltage of line 35 remains above 550 volts. Junction 483 is held at some predetermined voltage, for example, 6.0 volts by zener diode 484 over a broad range of electrical line 35 voltages, for example, 6.0 to 1,500 volts. Resistors 486 and 488 form a voltage divider, thus determining the voltage at junction 487—the junction 487 voltage bears the same relation to the electrical line 35 voltage as the resistive value of resistors 486 and 488. By a proper selection of the resistive values of resistors 486 and 488 the voltage on electrical line 35 which is required to establish a voltage at junction 487 sufficient to render transistor 490 conductive can be easily set at 550 volts.

Level detector 480 is electrically connected in controlling relation to reed relay 420. More particularly, the cathode 495 of transistor 490 is electrically connected to the coil 430 of reed relay 420 through Darlington amplifier 435. The electrical signal produced at cathode 495 of transistor 490 when transistor 490 becomes conductive is transmitted to, and sufficient for activating Darlington amplifier 435. This will cause current to flow through coil 430 of reed relay 420, thus switching reed switch 422 from terminal A to terminal B.

The element denoted level detector 460, is elementally and functionally quite similar to that of level detector 480. Level detector 460 comprises programable unijunction transistor (PUT) 470, zener diode 464, transistor 478, and resistors 462, 466, 468, 472 and 474. PUT 470 is similar to the PUT 490 of level detector 480. Resistor 462 and zener diode 464 are electrically connected in series between electrical line 35 and the system ground. Resistors 466 and 468, and the parallel combination of resistor 474 and transistor 478 are likewise connected in series between electrical line 35 and the system ground. Transistor 478 is connected with its collector 481 connected to the junction between resistors 468 and 474 and its emitter 477 connected directly to the system ground. The junction between resistor 462 and zener diode 464 for convenience denoted junction 463 is electrically connected to the gate 471 of PUT 470—the junction between resistors 466 and 468 for convenience denoted junction 467 is electrically connected to the anode 473 of PUT 470. The cathode 475 is electrically connected to Darlington amplifier 445 and to the system ground through resistor 472.

Level control 460 is voltage sensitive. It will be rendered active when the voltage on electrical line 35 is above some predetermined level, for example 900 volts. The junction 463 voltage is held at some predetermined value, for example, 6.0 volts by zener diode 464. A voltage of a predetermined amount, for example, 0.7 volts above the junction 463 voltage is required to render PUT 470 conductive. The junction 467 voltage bears the same relation to the electrical line 35 voltage as the resistive value of the series combination of resistor 468 and the parallel combination of resistor 474 and transistor 478 bears to the resistive value of the series combination of resistors 466, 468, and the parallel combination of resistor 474 and transistor 478. The resistive value of the parallel combination of resistor 474 and transistor 478 will, of course, be greater when transistor 478 is in the non-conductive state than when it is in the conductive state. Thus, the resistance of the series combination of resistor 468 and the parallel combination of resistor 474 and transistor 478 will be larger in relation to the resistance of the series combination of resistors 466 and 468 and the parallel combination of resistor 474 and transistor 478 when transistor 478 is non-conducting, than when it is conducting. Accordingly, for any given electrical line 35 voltage, the voltage at junction 467 will be greater when transistor 478 is non-conductive than when transistor 478 is conductive. The resistive values of transistors 466, 468 and 474 may be selected, so that the electrical line 35 voltage required to render PUT 470 conductive is 700 volts when transistor 478 is nonconductive, and 900 volts when transistor 478 is conductive. The normal state of transistor 478 is the nonconductive state.

Level control 460 is electrically connected in controlling relation to SCR 410. Specifically, cathode 475 of PUT 470 of level control 460 is connected through Darlington amplifier 445 and Photo-Darlington amplifier 440 to the gate 415 of SCR 410. The electrical signal produced at cathode 475 of PUT 470 when PUT 470 is rendered conductive is amplified and processed by Darlington amplifiers 445 and 440. The amplified and processed signal is transmitted to SCR gate 415 and is capable of causing SCR 410 to conduct. Accordingly, SCR 410 conducts when level detector 460 is active and level detector 460 is active when the voltage on electrical line 35 reaches 700 volts if transistor 478 is non-conductive, but does not become active until the electrical line 35 voltage reaches 900 volts if transistor 478 is conductive. Since reed switch 422 will normally be in position B when the voltage on electrical line 35 is above 550 volts, whenever SCR 410 conducts, a cardioverting pulse will be applied to the patient's heart.

Still with reference to FIG. 7, the element denoted 590 is a conventional binary counter. In a preferred embodiment, an RCA-CD4004E COS/MOS seven-stage Binary Counter is used. Functionally speaking, it will provide a different output signal for each electrical signal it receives. In a preferred embodiment an input 591 to counter 590 is electrically connected to the cathode 475 of PUT 470. Thus, each time PUT 470 is rendered conductive, the electrical signal produced at cathode 475 of PUT 470 is transmitted to input 591 of counter 590. Output terminal 595 is electrically connected to junction 335 of controller 30 via electrical line 19. When four electrical signals have been received at input terminal 591 of counter 590, an electrical signal will be provided at terminal 595 of counter 590. This electrical signal keeps junction 335 at a voltage sufficiently high so that controller 30 is disabled. Controller 30 cannot now activate DC—DC converter 32. Terminal 596 of counter 590 is connected to a reset circuit 500. When a positive electrical pulse is received at terminal 596, counter 590 will be reset to the "zero" state (the state in which there is no output signal from counter 590).

In the preferred embodiment the counter 590 is electrically connected via output terminals 592, 593 and 594 to the base 479 of transistor 478 in such a manner that the signal from counter 590 corresponding to each and every electrical input signal at input terminal 591 will render transistor 478 conductive.

As discussed above, the conduction or nonconduction of transistor 478 determines whether the cardioverting pulse applied to the heart is of a 700 or a 900 voltage magnitude. Transistor 478 is nonconductive when counter 590 is in the "zero" state and conductive when counter 590 is in any other state. Accordingly, the first cardioverting pulse applied to the patient's heart will have a 700 volt magnitude, and if that does not restore normal heart activity each succeeding pulse will have a 900 volt magnitude.

Reset circuit 500 comprises inverters 510, 530 and 550, diode 512, resistors 514 and 526, capacitor 516, transistor 520 and "nand" gate 540. The inverters and the "nand" gate are of conventional design. The input of inverter 510 is electrically connected to the cathode 475 of PUT 470 and the output is electrically connected to one side of diode 512. The other side of diode 512 is electrically connected to input terminal 542 of "nand" gate 540. It is also electrically connected through resistor 514 to the 4 volt power supply and through capacitor 516 to the system ground. Transistor 520 is connected having its base 521 electrically connected to electrical line 15, its emitter 525 electrically connected to the system ground, and its collector 523 electrically connected through resistor 526 to the 4 volt power source. The emitter 523 of transistor 520 and one side of resistor 526 are electrically connected to the input side of inverter 530. The output side of inverter 530 is connected to input terminal 544 of "nand" gate 540. The output terminal 546 of "nand" gate 540 is electrically connected through inverter 550 to input terminal 596 of counter 590.

Reset circuit 500 will reset counter 590 to the "zero" state whenever an electrical pulse corresponding to a normal heartbeat is received from sensing circuit 10 on electrical line 15. Circuit 500 is capable of differentiating between the heart activity associated with a normal heartbeat and the activity induced by a cardioverting pulse being applied to the heart. Circuit 500 is nonresponsive to the induced heart activity, but responsive to the normal heart activity and capable of resetting counter 590 to the "zero" state in response thereto.

Each electrical pulse corresponding to a normal heartbeat produced by sensing circuit 10 is transmitted to the base 521 of transistor 520. This pulse causes transistor 520 to conduct which allows current to flow through resistor 526 and transistor 520 to the system ground as long as transistor 520 is conductive, and thus lowers the voltage at the input 531 of inverter 530 for this time period. This negative pulse is inverted into a positive pulse by inverter 530 and transmitted to input 544 of "nand" gate 540. "Nand" gate 540 will invert this pulse and transmit the inverted pulse to inverter 550, provided the voltage at input 542 is not decreased. The voltage at input 542 is decreased only when a pulse is received from an active level detector 460 which occurs only when a cardioverting pulse is applied to the patient's heart. Specifically, when level detector 460 is active a positive pulse of short duration is transmitted to inverter 510 where it is inverted and transmitted on through diode 512. This negative pulse being transmitted through diode 512 allows capacitor 516 to discharge thus decreasing the voltage input at terminal 542 of "and" gate 540 for a period of time equal to the time required to recharge capacitor 516 from the 4 volt power source through resistor 514. This period of time typically is of a long enough duration so that it keeps the voltage at terminal 542 depressed during the time in which the heart activity induced by the cardioverting pulse is exhibited.

Inverter 550 inverts the negative pulse received from gate 540 into a positive pulse which is transmitted to the input 596 of counter 590. This pulse is sufficient to reset counter 590 to the "zero" state. In this manner, reset circuit 500 differentiates between a normal heart activity and the activity induced by a cardioverting pulse and resets counter 590 to the "zero" state when the heart activity is normal.

The apparatus of this invention comprises a sensing means 10 for monitoring heart activity and a stimulation means 12 for applying a shock to the patient's heart of sufficient magnitude to restore normal heart activity. The sensing means 10 controls the stimulation means 12 allowing the stimulation means 12 to apply a cardioverting shock to the heart only after normal heart activity has ceased. Upon monitoring life threatening arrhythmias, the apparatus of this invention automatically cardioverts the patient's heart.

As shown in FIG. 1, sensing means 10 includes EKG sensor 20, contraction sensor 22, "or" gate 24, and wave conformer 26. The EKG sensor 20 amplifies the R wave signal detected by electrical lead 16 corresponding to normal sinus rhythm of the human heart and filters out all other heart electrical activity. The contraction sensor 22 is responsive to the heart contractions detected by electrical lead 16 and is adapted to provide an electrical signal corresponding to each heart contraction. Gate 24 is constructed so that it provides an electrical output signal whenever it receives an electrical signal from either the contraction sensor 22 or the EKG sensor 20, or both. Consequently, if either the contraction sensor 22, relying on detected heart contraction, or the EKG sensor 20, relying on detected R waves or both provide an electrical signal to gate 24 corresponding to a normal heartbeat, gate 24 will provide an electrical signal in the form of a pulse corresponding to the heartbeat. Wave conformer 26 is adapted to transform these electrical pulses received from gate 24 which have varying amplitudes and widths into pulses having substantially the same pulse width and amplitude. Accordingly, sensing means 10 is responsive to each normal sinus heartbeat—detected by intravascular electrical lead 16 in the form of an R wave or as a heart contraction—and is adapted to provide an electrical pulse having a predetermined pulse amplitude and pulse width corresponding with each detected heartbeat.

Stimulation means 12 is adapted to apply electrical pulses to the heart via intravascular lead 16 for cardioverting a malfunctioning heart. These cardioverting pulses are not applied immediately upon the sensing of abnormal heart functioning, but their application is delayed for a period of time. This delay gives the heart the opportunity to convert to normal heart functioning, if it is able to do so. Stimulation means 12 applies a cardioverting pulse having a low energy content first, and then, if that pulse does not restore normal heart functioning, cardioverting pulses having higher energy content will be applied until the heart resumes normal functioning or the cardioverter is automatically disabled.

As shown in FIG. 1, stimulation means 12 includes controller 30, DC—DC converter 32, capacitor 34, regulator 36, and alert system 40. Stimulation means 12 is electrically connected to sensing means 10 by an electrical connection between wave conformer 26 of sensing means 10 and controller 30 of stimulation means 12 and to intravascular lead 16 via electrical line 17.

Controller 30 functions much like a timing device. Specifically, it provides an electrical signal if a predetermined period of time, for example, 5 seconds has elapsed without an electrical signal being received from wave conformer 26. Controller 30 continues to supply an electrical signal until it receives an electrical signal from wave conformer 26 corresponding to normal heart functioning. This electrical signal activates alert system 40 comprising both a visual and an audio alarm and activates DC—DC converter 32. Converter 32 is electrically connected to capacitor 34 and capable of charging capacitor 34 to a 1,000 volt level.

Converter 32 is a DC—DC converter of conventional design which is capable of increasing the power supply 33 voltage from 6 volts to 1,000 volts. Voltages in the 700–1,000 volt range are necessary to charge capacitor storage means 34 to a sufficient level so that it is capable of providing cardioverting pulses of the necessary magnitude. It takes a predetermined period of time, for example 10–15 seconds, to charge capacitor means 34 to the necessary level. However, any normal heartbeat during this interval will deactivate controller 30 which will then disable converter 32 and thus stop the charging cycle of energy storage means 34.

Accordingly, capacitor 34 is charged to the level required for cardioverting within 15–20 seconds (five second delay in controller 30 plus the 10–15 seconds needed to charge capacitor 34) following the last sensed normal heartbeat.

Regulator 36—electrically connected between capacitor 34 and intravascular lead 16—controls the application of energy from capacitor 34 to the patient's heart. It determines the energy content of the applied pulses, allowing only pulses to be applied when they have an energy content which is likely to be sufficient to stimulate heart activity.

Figure 8:
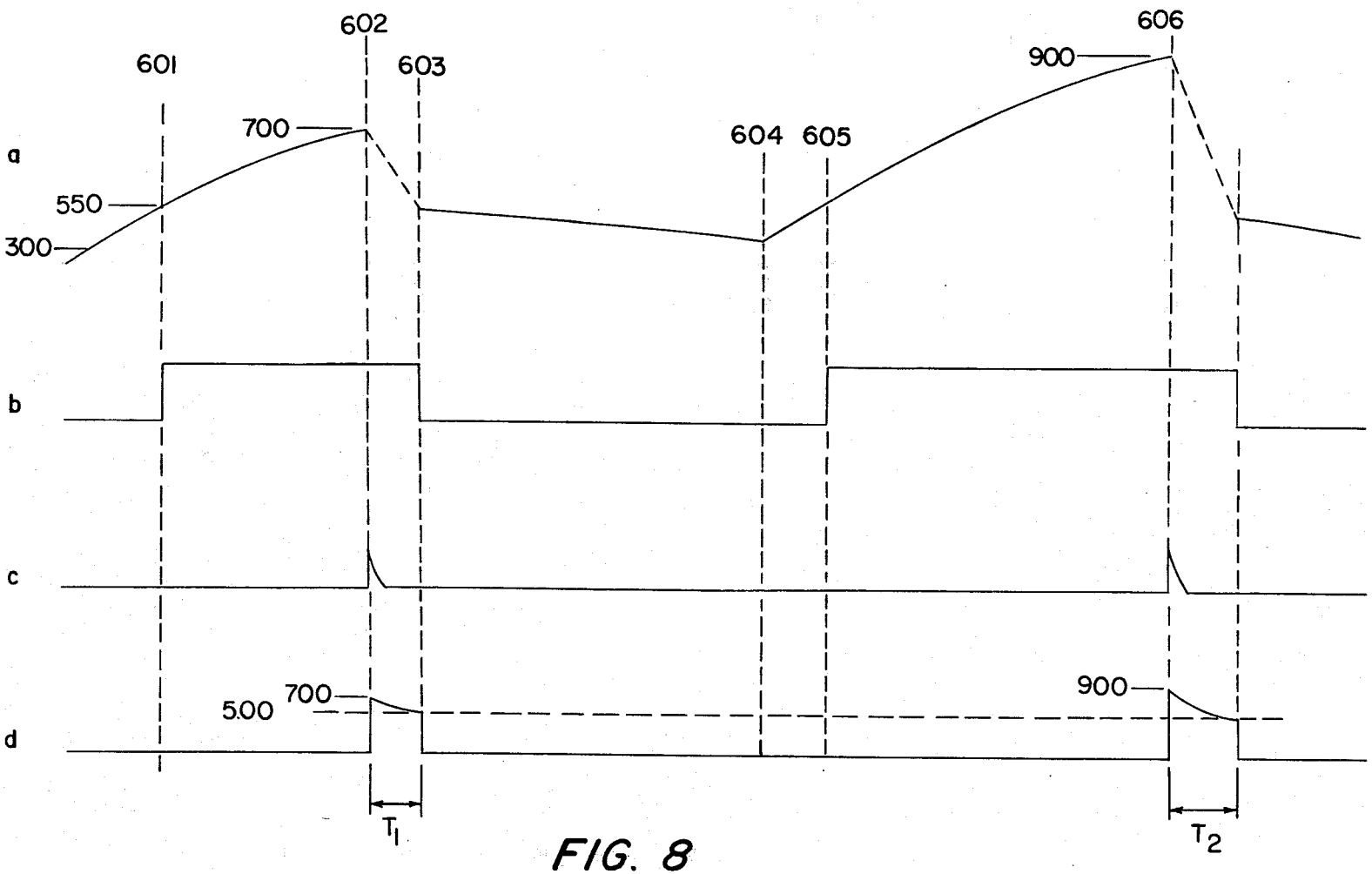
FIG. 8 is a voltage v. time diagram illustrating the voltage on the energy storage means embodied in the inventive apparatus and the states of the reed switch and the SCR embodied in the inventive apparatus, and how these voltages and component states effect the wave form and voltage magnitude of the cardioverting pulses applied to the patient's heart by the apparatus of [this] *the above-stated related* invention.

The functional operation of stimulation means 12 can be best described with reference to the voltage diagram of FIG. 8—a chronological description of the operation is possible using this diagram in explaining the differences between the first pulse generated and succeeding pulses. All times and waveforms are merely illustrative—the actual times and waveforms depend upon the particular components and component values used. FIG. 8 shows the voltage waveforms representing the voltage on capacitor 34, the state of reed switch 422, the state of SCR 410, and the voltage applied to the patient's heart. Specifically, waveform (a) shows the voltage on capacitor 34 as represented by the electrical line 35 voltage; waveform (b) shows the times when a voltage is applied across coil 430 of reed relay 420 as represented by the voltage at cathode 495 of control PUT 490 in regulator 36; waveform (c) shows the times when a voltage signal is applied to gate 415 of SCR 410 as represented by the voltage at cathode 475 of PUT 470 in regulator 36; and waveform (d) shows the voltage waveform of the pulse applied to the patient's heart as represented by the voltage at electrical line 17.

The active operation of stimulation means 12 begins when a pulse representing normal heart activity has not been received from sensing means 10 for 5 seconds. When this occurs controller 30 becomes active supplying an electrical signal to converter 32. Converter 32 becomes active and charges capacitor 34. It takes converter 32 approximately 9 seconds to charge capacitor 34 to the 550 volt level. When capacitor 34 becomes charged to the 550 volt level (line 601 in FIG. 8) PUT 490 of level control 480 becomes active thus switching reed relay 420 to position B. It takes converter 32 an additional three seconds to charge capacitor 34 to the 700 volt level. When this occurs (line 602 in FIG. 8) PUT 470 of level control 460 becomes active thus rendering SCR 410 conductive. With reed switch 422 in position B and SCR 410 conductive, capacitor 34 has a discharge path through the patient's heart. Capacitor 34 begins to discharge immediately upon SCR 410 being rendered conductive (line 602, FIG. 8) and discharges through the patient's heart until reed switch 422 is switched to position A (line 603, FIG. 8). Reed switch 422 is switched to position A when the capacitor 34 voltage is reduced to the 500 volt level. Accordingly, 17 seconds (5 sec. + 9 sec. + 3 sec.) following the last sensed normal heart activity a cardioverting pulse is applied to the patient's heart. This cardioverting pulse is in a truncated capacitive discharge waveform having a peak magnitude of 700 volts and being truncated at the 500 volt level.

If this first cardioverting pulse stimulates normal heart activity, sensing means 10 senses the resumed normal heart activity and disables stimulation means 12—but if this first pulse did not stimulate normal heart activity, a second cardioverting pulse is needed and is supplied by stimulation means 12. Assuming that normal heart activity has not been restored, controller 30 will become active again 5 seconds following the first cardioverting pulse. This occurs since the contraction sensing portion of sensing means 10 is responsive to the heart contraction caused by the cardioverting pulse. The pulse it generates which corresponds with the cardioverting pulse deactivates controller 30. It takes 5 seconds for controller 30 to be activated again. Capacitor 34 is still charged to nearly 500 volts 5 seconds after the first cardioverting pulse (line 604, FIG. 8). Thus it will take only 1 second to charge capacitor to the 550 volt level necessary to switch reed switch 420 to position B (line 605, FIG. 8). However, 900 volts are now required to render SCR 410 conductive instead of the 700 volts required for the first pulse. This is due to transistor 478 in SCR level control 460 being rendered conductive as a result of the first applied pulse. It takes approximately 5 seconds to charge capacitor 34 to the 900 volt level required to render SCR 410 conductive (line 606, FIG. 8). Once the 900 volt level is reached SCR 410 becomes conductive and capacitor 34 discharges until reed switch 422 is switched to position A. Accordingly, 11 seconds (5 sec. + 1 sec. + 5 sec.) after the first cardioverting pulse a second cardioverting pulse also having a truncated capacitive discharge waveform is applied to the heart.

The second applied pulse has a greater energy content than the first pulse. The energy content is greater as the peak voltage of the second pulse (900 volts) is greater than the peak voltage of the first pulse (700 volts) and both pulses truncate at 500 volts.

If the second cardioverting pulse stimulates normal heart activity, sensing means 10 will sense this and disable stimulation means 12. If not, a third cardioverting pulse which is similar to the second pulse will be applied in a manner similar to that of the second pulse. If the third pulse still does not restore normal heart functioning, stimulation means 12 will be disabled automatically.

Although the invention has been described with reference to a particular embodiment, it will be understood that this embodiment is merely illustrative of the applications of the principles of this invention. It will be further understood that numerous modifications in the inventive embodiment may be made and other arrangements may be devised without departing from the spirit and scope of this invention.

By suitable modifications in the inventive circuitry many modifications in the functional operation of the invention can be achieved. For example, a P-wave amplifier could be used instead of the described R-wave amplifier in EKG sensor 20. A gating means which is nonresponsive to electrical signals having a repetitive rate greater than a predetermined amount could be used in place of or in addition to "or" gate 64 to discriminate against certain types of tachyarrhythmias and thus allow a cardioverting pulse to be applied when the heart is functioning in this manner. A dynamic heart characteristic such as heart pressure could be monitored instead of either EKG or heart contractions. Additionally, each cardioverting pulse could have an increased energy content; the time between cardioverting pulses could be decreased for additional applied cardioverting pulses; or the cardioverting pulse could be applied using an intravascular lead which is distinct from the intravascular lead which is used to sense heart activity.

Many substitutions may, of course, be made in the circuit elements used in the inventive circuit without materially affecting the operation of the invention. For example, two independent power sources could be used instead of having a 6 volt battery drive or 4 volt constant voltage source; various arrangements of SCR's and/or transformers as well as solid state switching devices could be used to control the transmission of the cardioverting pulse to the patient's heart instead of the particular arrangement of an SCR and a reed relay actually used; and devices of various types could be used to perform the level detecting function performed by level detectors 460 and 480. Many more examples are possible—the above listing is anything but exhaustive.

We claim:

1. Heart contraction sensing and stimulation circuit comprising:

a. first detecting means responsive to a change in a monitored electrical parameter produced by the normal beating action of the heart for providing a first identifiable electrical signal corresponding with each heart contraction;

b. second detecting means responsive to monitored heart electrical activity corresponding to heart contractions for providing a second identifiable signal corresponding with each heart contraction;

c. gating means electrically connected to receive electrical signals from said first and second detecting means, said gating means for providing an electrical output signal in response to either of said identifiable electric signals produced by a single heart contraction;

d. electrical energy storage means capable of storing sufficient energy to cardiovert a malfunctioning heart;

e. electrical energy source means;

f. control means connected in controlling relation to said energy storage means and said energy source means and operatively connected to said gating means and responsive thereto, said control means for controlling the transmission of electrical energy from said source means to said storage means only in the absence of electrical signals from both the first and second detecting means for a predetermined period of time;

g. output means adapted for connection to the heart;

h. regulating means connected in controlling relation to said energy storage means, said regulating means for permitting energy to be transmitted from said storage means to said output means when the energy stored by said storage means becomes greater than a predetermined level.

[2. Heat contraction sensing and stimulation apparatus comprising:

a. first heart monitoring means being in the form of an elastomer body means having conductive particles imbedded therein and exhibiting a change in electrical impedance upon flexing, the body means including means adapted to be positioned adjacent heart muscle so that each heart contraction causes the body means to flex thereby changing its impedance;

b. first detecting means responsive to a change in impedance of said elastomer body means for providing a first identifiable electrical signal corresponding with each heart contraction;

c. second heart monitoring means in the form of conductive electrode means being adapted for insertion within the human vascular system and positioned adjacent the heart for monitoring heart electrical activity and transmitting electrical energy to the heart, d. second detecting means responsive to the monitored heart electrical activity corresponding to heart contractions for providing a second identifiable signal corresponding with each heart contraction;

e. gating means electrically connected to receive electrical signals from said first and second detecting means, said gating means for providing an electrical output signal in response to either of said identifiable electrical signals produced by a single heart contraction;

f. electrical energy storage means capable of storing sufficient energy to cardiovert a malfunctioning heart;

g. electrical energy source means;

h. control means electrically connected in controlling relation to said energy storage means and said energy source means and operatively connected to said gating means and responsive thereto, said control means for controlling the transmission of electrical energy from said source means to said storage means only in the absence of both said first and second identifiable signals for a predetermined period of time;

i. regulating means electrically connected to said electrode means and further connected in controlling relation to said energy storage means, said regulating means for permitting transmission of energy from said storage means to said electrode means when the energy stored by said storage means is greater than a predetermined level; and j. disabling means electrically connected to said first monitoring means for sensing a break in the electrical circuitry of said first monitoring means, said disabling means for preventing electrical energy from being delivered to said electrodes when such a break occurs.]

[3. The apparatus of claim 2 further comprising flexible enclosure means substantially inert in living body fluids and tissue, the enclosure means being adapted for insertion within the vascular system of a living animal, the enclosure means further for enclosing, at least some of, the apparatus elements, thereby sealing them from living body fluids and tissues.]

[4. The apparatus of claim 2 wherein the second monitoring means includes two conductive electrode means, one of the electrode means being adapted to be positioned within the heart and the other electrode means being adapted to be positioned outside the heart to monitor heart electrical activity produced by the natural beating action of the heart.]

[5. The apparatus of claim 2 wherein the second detecting means includes discrimination means, said discrimination means for responding to the heart electrical activity produced by the natural beating action of the heart while discriminating against the heart electrical signals produced by an abnormally functioning heart and those artificially induced by a heart pacing device.]

[6. The apparatus of claim 2 wherein said gating means includes a conforming means, said conforming means for transforming the pulses having varying amplitudes and widths into pulses having substantially the same pulse amplitude and pulse width.]

[7. The apparatus of claim 2 wherein said control means has a transmitting and a non-transmitting state and includes a timing means for maintaining said control means in the non-transmitting state for a predetermined time interval following each signal received from said gating means.]

[8. The apparatus of claim 7 wherein the timing means includes capacitive means for switching said control means from the non-conductive state to the conductive state when said capacitive means becomes charged above a predetermined level, said capacitive means being operatively connected to said gating means so that a signal from said gating means causes the capacitive means to discharge rendering said control means non-conductive.]

[9. The apparatus of claim 2 further comprising a counting means operatively connected to said energy storage means for disabling the transmission of electrical pulses from said energy storage means to said electrode means after a predetermined number of electrical pulses have been transmitted without an intervening heart contraction having been detected by said first or second detecting means.]

[10. The apparatus of claim 2 wherein the regulating means includes multiple level control means, said level control means being constructed and arranged such that energy will begin being transmitted from said energy storage means to said electrodes when the energy stored by said storage means is above a certain first predetermined level and will cease being transmitted when the stored energy becomes less than a second lesser predetermined level, thereby causing the energy stored by said storage means to be transmitted to said electrodes in a truncated capacitive discharge electrical pulse waveform.]

[11. The apparatus of claim 2 wherein the regulating means includes means for setting the time interval between the generation of the latest pulse from said gate means and the generation of the first electrical pulse transmitted to said electrode means so that said time interval is substantially greater than the time interval between each of the succeeding electrical pulses transmitted to said electrodes, during the time interval in which no pulses are provided by said gate means.]

[12. The apparatus of claim 2 wherein the regulating means includes means for increasing the energy content of all but the first electrical pulse of the series of pulses transmitted to said electrodes during the time interval in which there is an absence of normal heart contractions.]

[13. In an automatic cardioverting system comprising intravascular electrical lead means having electrodes adapted for transmitting electrical pulses to the heart of a living animal, sensing means including electrically conductive means within said lead means and flexible therewith for sensing the action of a heart contration upon said lead means, means electrically connected with and responsive to said sensing means for continuously monitoring heart activity and producing an identifiable electrical signal corresponding to each sensed heart contraction, and stimulation means responsive to the identifiable signal and operatively connected to said intravascular lead for providing cardioverting shocks to said electrodes, the improvement comprising:

disabling means electrically connected to said sensing means for sensing a break in said electrically conductive means, and its electrical connection with said monitoring means, said disabling means for preventing cardioverting shocks from being transmitted from said stimulating means to said electrode upon sensing a break in said electrically conductive means or its electrical circuitry.]

* * * * *